United States Patent
Hsieh et al.

(10) Patent No.: US 10,013,780 B2
(45) Date of Patent: Jul. 3, 2018

(54) SYSTEMS AND METHODS FOR ARTIFACT REMOVAL FOR COMPUTED TOMOGRAPHY IMAGING

(71) Applicants: General Electric Company, Schenectady, NY (US); Wisconsin Alumni Research Foundation, Madison, WI (US)

(72) Inventors: Jiang Hsieh, Waukesha, WI (US); GuangHong Chen, Madison, WI (US)

(73) Assignees: General Electric Company, Schenectady, NY (US); Wisconsin Alumni Research Foundation, Madison, WI (US)

( * ) Notice: Subject to any disclaimer, the term of this patent is extended or adjusted under 35 U.S.C. 154(b) by 12 days.

(21) Appl. No.: 15/056,657

(22) Filed: Feb. 29, 2016

(65) Prior Publication Data
US 2017/0249759 A1    Aug. 31, 2017

(51) Int. Cl.
| | |
|---|---|
| *G06K 9/00* | (2006.01) |
| *G06T 11/00* | (2006.01) |
| *G06K 9/62* | (2006.01) |
| *G06T 5/50* | (2006.01) |
| *G06T 7/00* | (2017.01) |

(Continued)

(52) U.S. Cl.
CPC ............ *G06T 11/008* (2013.01); *A61B 6/032* (2013.01); *A61B 6/5258* (2013.01); *G06K 9/6255* (2013.01); *G06T 5/50* (2013.01); *G06T 7/0012* (2013.01); *G06T 7/0081* (2013.01); *G06T 2207/10081* (2013.01); *G06T 2207/20021* (2013.01); *G06T 2207/20224* (2013.01); *G06T 2211/421* (2013.01); *G06T 2211/432* (2013.01)

(58) Field of Classification Search
CPC ................. G06T 11/008; G06T 2207/20224
See application file for complete search history.

(56) References Cited

U.S. PATENT DOCUMENTS

| | | | |
|---|---|---|---|
| 4,189,775 A | 2/1980 | Inouye et al. | |
| 4,602,348 A | 7/1986 | Heat | |

(Continued)

OTHER PUBLICATIONS

U.S. Patent and Trademark Office, U.S. Appl. No. 14/663,864, filed Mar. 20, 2015.

*Primary Examiner* — Oneal R Mistry
(74) *Attorney, Agent, or Firm* — Dean D. Small; The Small Patent Law Group, LLC

(57) ABSTRACT

An imaging system includes a computed tomography (CT) acquisition unit and at least one processor. The CT acquisition unit includes an X-ray source and a CT detector configured to collect CT imaging data of an object. The at least one processor is operably coupled to the CT acquisition unit, and configured to reconstruct an initial image using the CT imaging information, the initial image including at least one object representation portion and at least one artifact portion; identify at least one region of the initial image containing at least one artifact and isolate the at least one artifact by analyzing the initial image using an artifact dictionary and a non-artifact dictionary, the artifact dictionary including entries describing corresponding artifact image portions, the non-artifact dictionary including entries defining corresponding non-artifact image portions; and remove the at least one artifact from the initial image to provide a corrected image.

15 Claims, 6 Drawing Sheets

(51) Int. Cl.
*A61B 6/00* (2006.01)
*A61B 6/03* (2006.01)

(56) References Cited

U.S. PATENT DOCUMENTS

| | | |
|---|---|---|
| 4,751,644 A | 6/1988 | Koka et al. |
| 4,809,172 A | 2/1989 | Hopkinson et al. |
| 5,128,864 A | 7/1992 | Waggener et al. |
| 5,140,520 A | 8/1992 | Matsumura |
| 5,229,934 A | 7/1993 | Mattson et al. |
| 5,243,664 A | 9/1993 | Tuy |
| 5,271,055 A | 12/1993 | Hsieh et al. |
| 5,355,310 A | 10/1994 | Brunner |
| 5,361,291 A | 11/1994 | Toth et al. |
| 5,400,255 A | 3/1995 | Hu |
| 5,473,655 A | 12/1995 | Hu |
| 5,473,656 A | 12/1995 | Hsieh et al. |
| 5,757,951 A | 5/1998 | Tuy |
| 6,628,744 B1 | 9/2003 | Luhta et al. |
| 6,639,965 B1 | 10/2003 | Hsieh et al. |
| 8,364,244 B2 | 1/2013 | Angelos et al. |
| 2011/0110572 A1* | 5/2011 | Guehring ............ A61B 6/5258 382/131 |
| 2013/0222430 A1* | 8/2013 | Bredno ................ G06T 7/0014 345/634 |
| 2016/0007948 A1* | 1/2016 | Isola .................... A61B 6/032 382/131 |
| 2017/0039706 A1* | 2/2017 | Mikhno ............... A61B 6/037 |

* cited by examiner

SYSTEMS AND METHODS FOR ARTIFACT REMOVAL FOR COMPUTED TOMOGRAPHY IMAGING

BACKGROUND OF THE INVENTION

The subject matter disclosed herein relates generally to systems and methods for imaging, for example to systems and methods for reducing artifacts in computed tomography (CT) images.

In CT imaging, an X-ray source may be rotated around an object to obtain imaging information. X-rays from the source attenuated by the object may be collected or detected by a detector and used to reconstruct an image.

In modern CT imaging, there are a number of non-ideal physical conditions that may cause artifacts in reconstructed CT images. Mitigation or elimination of image artifacts has been a time and resource consuming issue for medical imaging devices. Certain conventional approaches have been aimed at improving data acquisition hardware so that that acquired data is more consistent with underlying imaging models, or to incorporate a model of a non-ideal acquisition process into a calibration and/or reconstruction process. Such approaches are strongly dependent on the data acquisition methods and the underlying physical and engineering principles.

BRIEF DESCRIPTION OF THE INVENTION

In one embodiment, an imaging system is provided that includes a computed tomography (CT) acquisition unit and at least one processor. The CT acquisition unit includes an X-ray source and a CT detector configured to collect CT imaging data of an object to be imaged. The X-ray source and CT detector are configured to be rotated relative to the object to be imaged and to collect a series of projections of the object as the X-ray source and CT detector rotate relative the object to be imaged. The at least one processor is operably coupled to the CT acquisition unit, and configured to reconstruct an initial image using the CT imaging information, the initial image including at least one object representation portion and at least one artifact portion; identify at least region of the initial image including at least one artifact, and isolate the at least one artifact from desired image content by analyzing the initial image using an artifact dictionary and a non-artifact dictionary (which may be referred to as sub-dictionaries of a discriminative dictionary), the artifact dictionary including entries (or atoms) describing corresponding artifact image portions, the non-artifact dictionary including entries (or atoms) defining corresponding non-artifact image portions; and remove the at least one artifact from the initial image to provide a corrected image.

In another embodiment, a method is provided that includes acquiring imaging information of an acquisition volume of an object. The method also includes reconstructing an initial image using the imaging information. The initial image includes at least one object representation portion and at least one artifact portion. Further, the method includes identifying at least one region of the initial image containing at least one artifact along with desired imaging information (e.g., the at least one object representation portion). The at least one artifact is isolated from desired image content by analyzing the initial image using an artifact dictionary and a non-artifact dictionary. The artifact dictionary includes entries describing corresponding artifact image portions, and the non-artifact dictionary includes entries defining corresponding non-artifact image portions. Also, the method includes removing the at least one artifact from the initial image to provide a corrected image.

In another embodiment, a tangible and non-transitory computer readable medium is provided that includes one or more computer software modules configured to direct one or more processors to: acquire imaging information of an acquisition volume of an object; reconstruct an initial image using the imaging information, where the initial image includes at least one object representation portion and at least one artifact portion; identify at least one region of the initial image containing at least one artifact along with desired imaging information and isolate the at least one artifact from desired image content by analyzing the initial image using an artifact dictionary and a non-artifact dictionary, wherein the artifact dictionary includes entries describing corresponding artifact image portions, and the non-artifact dictionary includes entries defining corresponding non-artifact image portions; and remove the at least one artifact from the initial image to provide a corrected image.

DETAILED DESCRIPTION OF THE INVENTION

Figure 1:
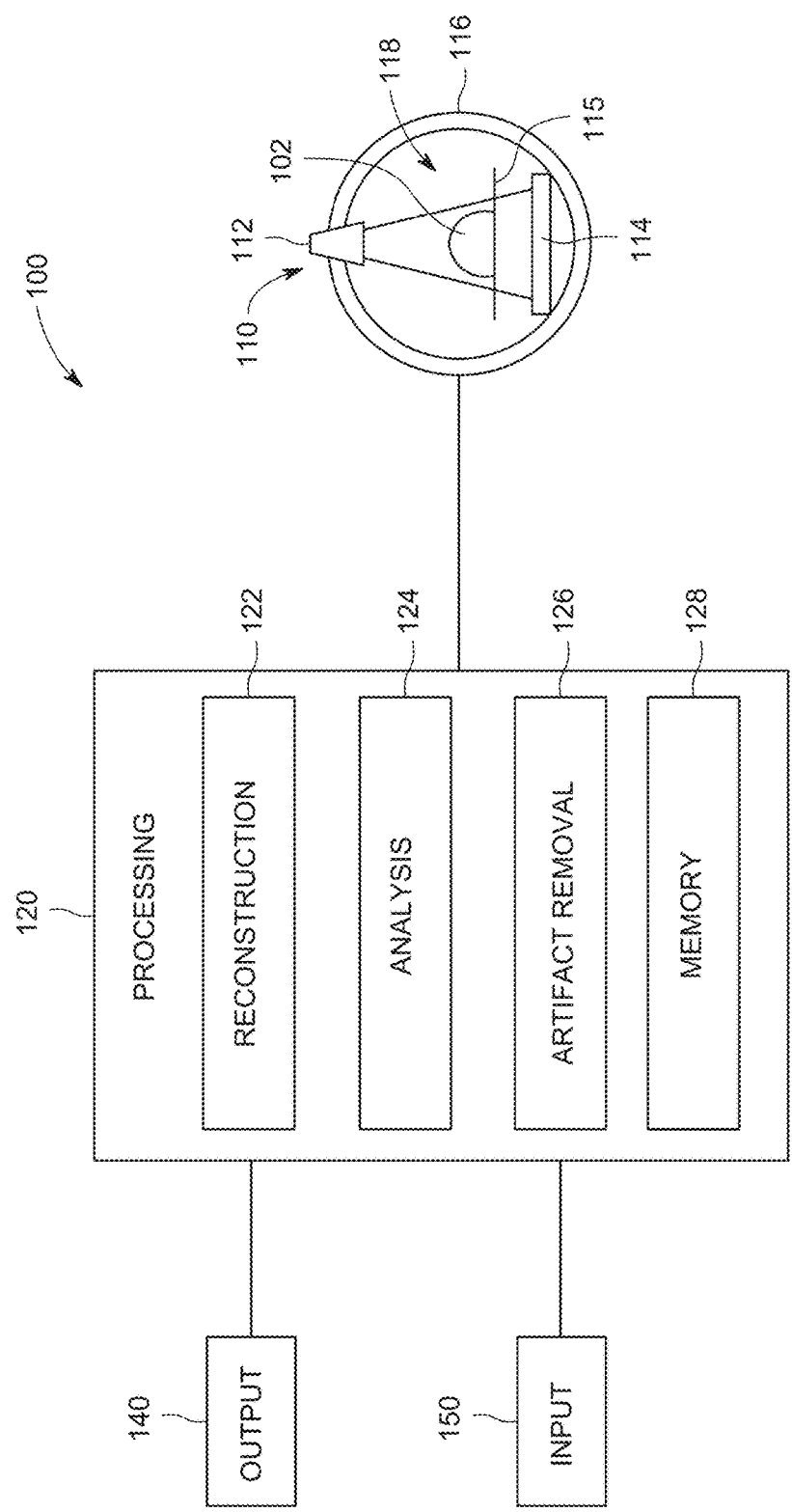
FIG. 1 is a schematic block diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should be further understood that the figures illustrate example embodiments of the present disclosure. Variations, such as replacing or modifying one or more functional blocks, are possible to achieve similar results.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also used herein, the phrase "reconstructing an image" is not intended to exclude embodiments in which data representing an image is generated, but a viewable image is not. As used herein, the term "image" broadly refers to both viewable images and data representing a viewable image. It may be noted that various embodiments generate, or are configured to generate, at least one viewable image.

Various embodiments provide systems and methods for identification and/or removal of artifacts including recurring artifacts (e.g., artifacts recurring along a longitudinal direction of an image caused by off-focal radiation). Various embodiments provide systems and methods for decomposing an artifact-contaminated image into two sub-images: a first sub-image that is entirely or primarily artifacts, and a second sub-image that is an artifacts mitigated image or target outcome.

Various embodiments may include two primary steps or actions. The first is to divide an image into many small patches, which may be overlapping in some embodiments or non-overlapping in other embodiments. The size and/or location of the patches may be anatomy- and/or location-dependent. The second is to decompose each small patch into two sub-patches with one sub-patch corresponding to one or more artifacts and the other being devoid of one or more artifacts, or having reduced artifacts. In some embodiments, the decomposition process may be carried out solely based on the small patch itself, or based on combined information provided by the small patch and one or more neighboring or proximate patches. After each small patch is separated into artifacts and non-artifacts, the artifact patches and non-artifact patches may be recombined to generate an artifact image and an artifact-free image (or reduced artifact image). To separate each patch into two patches (e.g., two mutually exclusive patches) two dictionaries are constructed in various embodiments: a first dictionary, which is constructed to represent artifacts, and a second dictionary, which is a non-artifact dictionary. The projection of non-artifact components of image patches onto entries of the artifact dictionary may be negligible or zero, while the projection of artifacts onto entries of the non-artifact dictionary may be negligible or zero. Using such constructed dual dictionaries a priori, each small image patch may be decomposed into an artifact patch and a non-artifact patch. It may be noted that multiple passes or iterations may be made on a given patch or patches to remove more than one type of artifact.

In various embodiments, at least one region of an initial image containing at least one artifact is identified (e.g., a region of interest ROI), and the at least one artifact is isolated from desired image content by analyzing the ROI using an artifact dictionary and a non-artifact dictionary. The at least one artifact in various embodiments is isolated from desired image content by identifying a corresponding artifact entry from the artifact dictionary. Once identified or isolated, the at least one artifact may be removed by subtracting the at least one artifact (e.g., the selected artifact entry from the artifact dictionary) from the initial image (e.g., from a patch of the initial image).

Various different artifacts may be addressed in various embodiments. For example, in some embodiments, banding artifacts caused by off-focal radiation in volumetric CT exams may be addressed. In some embodiments, truncation artifacts which may occur in CT exams may be addressed. As another example, in some embodiments, residual Morie artifacts in x-ray phase contrast images may be addressed. Generally, the systems and methods disclosed herein may be applied to other imaging modalities than x-ray or CT where an adequate artifact dictionary may be constructed.

Various embodiments provide improved imaging. A technical effect of at least one embodiment includes reduction or elimination of artifacts. A technical effect of at least one embodiment includes reduction of hardware costs, for example costs associated with calibrating a system to attempt to address off-focal radiation or other potential sources of artifacts. A technical effect of at least one embodiment includes reduction of artifacts when projection data is unavailable.

FIG. 1 illustrates an imaging system 100 in accordance with an embodiment. The imaging system 100 may be configured, for example, to perform computed tomography (CT) scanning of an object, such as a human or animal patient (or portion thereof), such as CT scanning for a perfusion study. It may be noted that other imaging modalities may be employed additionally or alternatively in alternate embodiments. The imaging system 100 includes a CT acquisition unit 110 and a processing unit 120. Generally, the CT acquisition unit 110 is configured to acquire projection data or imaging data (e.g., CT data or CT imaging information), and the processing unit 120 is configured to reconstruct images using the data acquired by the CT acquisition unit 110. It may be noted that various embodiments may include additional components, or may not include all of the components shown in FIG. 1 (for example, various embodiments may provide sub-systems for use with other sub-systems to provide an imaging system). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted CT acquisition unit 110 includes an X-ray source 112 and a CT detector 114. (For additional information regarding example CT systems, see FIG. 6 and related discussion herein.) The X-ray source 112 and the CT detector 114 (along with associated components such as bowtie filters, source collimators, detector collimators, or the like (not shown in FIG. 1)) may rotate relative to the object to be imaged. For example, in some embodiments, the X-ray source 112 and the CT detector 114 may rotate about a central axis of a bore of a gantry 116 of the system 100. As another example (e.g., for small animal imaging), the X-ray source 112 and the CT detector 114 may be stationary, while the object spins or rotates about a fixed axis.

Generally, X-rays from the X-ray source 112 may be guided to an object 102 to be imaged through a source collimator and bowtie filter. The object 102 to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter may be configured to absorb radiation from the X-ray source 112 to control distribution of X-rays passed to the object to be imaged.

X-rays that pass through the object to be imaged are attenuated by the object 102 and received by the CT detector 114 (which may have a detector collimator associated therewith), which detects the attenuated X-rays and provides imaging information to the processing unit 120. The processing unit 120 may then reconstruct an image of the scanned portion of the object 102 using the imaging information (or projection information) provided by the CT detector 114. The processing unit 120 may include or be operably coupled to the output unit 140, which in the illustrated embodiment is configured to display an image, for example, an image reconstructed by the processing unit 120 using imaging information from the CT detector 114. The depicted input unit 150 is configured to obtain input corresponding to a scan to be performed, with the processing unit 120 using the input to determine one or more scan settings (e.g., tube voltage, tube current, scanning rotation speed, or the like). The input unit 150 may include a keyboard, mouse, touchscreen or the like to receive input from an operator, and/or may include a port or other connectivity device to receive input from a computer or other source.

In the illustrated embodiment, the X-ray source 112 is configured to rotate about the object 102. For example, the X-ray source 112 and the CT detector 114 may be positioned about a bore 118 of the gantry 116 and rotated about the object 102 to be imaged. As the X-ray source 112 rotates about the object 102 during an imaging scan, X-rays received by the CT detector 114 during one complete rotation provide a 360 degree view of X-rays that have passed through the object. Other imaging scanning ranges may be used in alternative embodiments. The CT imaging information may be collected as a series of views that together make up a rotation or portion thereof. Each view or projection may have a view duration during which information (e.g., counts) is collected for the particular view. The view duration for a particular view defines a CT information acquisition period for that particular view. For example, each rotation may be made up of about 1000 views or projections, with each view or projection having a duration or length of about $\frac{1}{1000}$ of a complete rotation. The X-ray source may be turned on and off to control the acquisition time. For example, to perform an imaging scan of a complete rotation, the X-ray source may be turned on at a particular rotational position of the gantry and turned off when the X-ray source returns to the particular rotational position after a complete rotation.

The imaging system 100 may be configured to acquire or collect CT information at plural imaging locations along a longitudinal direction. The imaging locations may be continuous (e.g., in a helical scan where a table or bed moves longitudinally with respect to one or more detectors during rotation) or discrete (e.g., in a step and shoot technique in which the table or bed does not move longitudinally with respect to one or more detectors during rotation, but instead is articulated longitudinally by a step or increment between rotations or information collection). An acquisition volume of the object 102 may be understood as being defined by the cross-section of the object 102 (e.g., the shape of the object in an x-y plane where a longitudinal direction is denoted as a z-direction) extending along the longitudinal direction. For example, in a step and shoot mode of operation, the X-ray source 112 and the CT detector 114 may be rotated about the object 102 while remaining stationary with respect to the object 102 along the longitudinal direction. After a desired amount of information is collected (e.g., a complete rotation), the X-ray source 112 and CT detector 114 may be advanced an increment (or step) D to collect additional imaging information at a second imaging location. As another example, in a helical mode of operation, the X-ray source 112 and the CT detector 114 may be rotated about the object 102 while also translating longitudinally with respect to the object 102 along the longitudinal direction. It may be noted the relative longitudinal movement of the table may be achieved by moving an X-ray source and detector while maintaining the table in a stationary longitudinal position, moving the table while maintaining the X-ray source and detector in a stationary longitudinal position, or moving both the table and the X-ray source and detector (e.g., at different speeds and/or in different directions relative to each other).

Generally, the processing unit 120 in various embodiments identifies artifacts using dictionaries including entries (which may be referred to as atoms) that correspond to known or previously encountered artifacts. After an artifact is identified using a comparison to entries of dictionaries, the artifact may be removed from an image.

The processing unit 120, in various embodiments, acquires CT imaging information from the acquisition unit 110 and reconstructs an initial image using the CT imaging information. For example, the CT imaging information may be acquired in projection space and transformed into a reconstructed image in image space. The initial image includes at least one object representation portion and at least one artifact portion.

The processing unit 120 next identifies at least one region of the initial image that includes at least one artifact, and isolates the at least one artifact by analyzing the initial image using an artifact directory and a non-artifact dictionary. The artifact dictionary includes entries describing corresponding artifact image portions. For example, known artifacts from previous images may be used to construct entries in the artifact dictionary. Additionally or alternatively, artifact dictionaries may be generated using phantom studies. For example, a phantom with a known corresponding true image may be imaged under conditions known to generate particular artifacts, such as banding due to off-focal radiation, and/or truncation artifacts at the edge of an image. Then, the artifact portion of an image (or portion thereof such as a patch) may be identified based on a comparison of the obtained image with the known true target outcome. The non-artifact dictionary includes entries defining corresponding non-artifact image portions. In some embodiments, the non-artifact image portion may correspond to a true or accurate representation of scanned anatomy, while in other embodiments the non-artifact image portion may correspond to random or uniformly distributed noise. Generally, the processing unit 120 may compare acquired image portions with various combinations of entries from the artifact dictionary and non-artifact dictionary to find a best fit. Then, the artifact dictionary entry of the combination that gives the best fit may be identified as an artifact in the initial image, and the artifact (e.g., the identified artifact dictionary entry or a weighted modification thereof) may be removed from the image. It may be noted that dictionary entries may be for particular patch sizes and/or locations as discussed herein, with portions of an image analyzed using dictionary entries from corresponding locations (e.g., portions of an image at an edge of an image may be analyzed based on dictionary entries corresponding to the edge).

The processing unit 120, after identifying and isolating the at least one artifact, removes the at least one artifact from the initial image to provide a corrected image. It may be noted that the corrected image may be further analyzed, for example using additional dictionaries to provide subsequent corrected images until a final image is generated. For example, if an image is known or suspected to be subject to two distinct artifacts, a first analysis using a first artifact dictionary may be performed on an initial image to remove the first type of artifact to provide a corrected image. Then, a second analysis using a second artifact dictionary may be performed on the corrected image to remove the second type of artifact to provide a further corrected image. In some embodiments, the first and second analysis may be performed at or around the same time, for example, if the types of artifacts are known to occur on different parts of an image. Then, the first part of the image may be analyzed using a first artifact dictionary while the second part of the image is analyzed using the second artifact dictionary.

Figure 2:
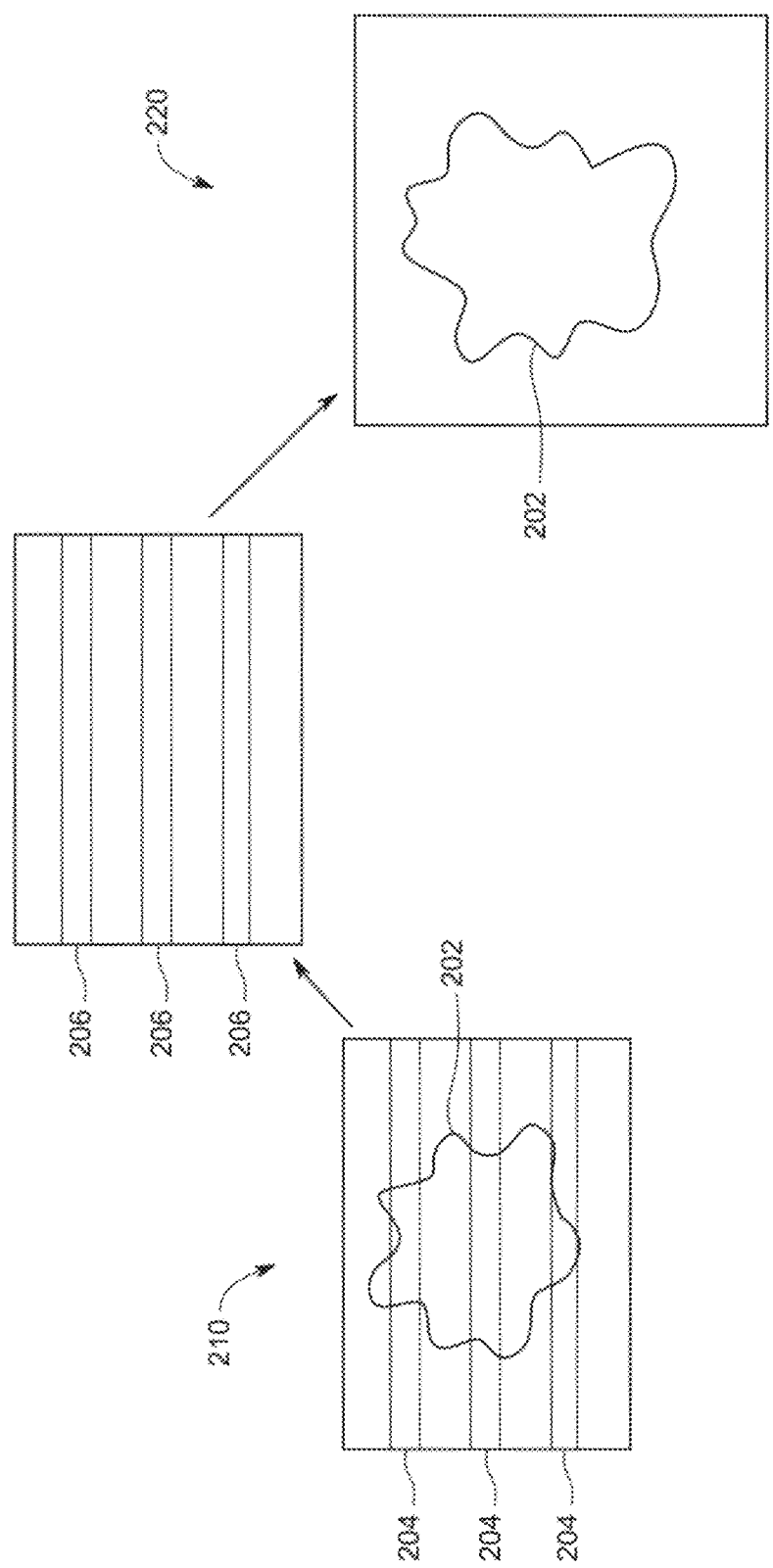
FIG. 2 provides a schematic representation of the removal of an artifact from an image in accordance with various embodiments.

FIG. 2 provides a schematic representation of the removal of an artifact from an image. As seen in FIG. 2, an initial image 210 includes an object representation portion 202 which corresponds to an object being imaged, and an artifact portion 204. The initial image 210 may be analyzed using dictionaries as discussed herein to identify an artifact dictionary entry 206 that most closely matches the artifact portion 204. The artifact dictionary entry 206 may then be removed from the initial image 210 to provide a corrected image 220 without the artifact portion 204. The more artifact portion entries and/or the more accurate or representative are the artifact portion entries of the dictionary, the more accurately the artifact portion 204 may be approximated by the selected artifact dictionary entry 206, and the more completely the artifact portion 204 may be removed from the corrected image 220. It may be noted that representation of FIG. 2 is provided for illustrative purposes and that various modifications may be utilized in different embodiments. For example, a selected entry from an artifact dictionary may be identified and/or applied using a weighting coefficient. As another example, in various embodiments, an initial image may be separated into smaller patches, with some or all of the patches analyzed independently of at least some other patches using dictionaries as discussed herein.

For example, in some embodiments, the processing unit 120 is configured to divide the initial image into plural patches. The patches may include overlapping portions with neighboring patches in some embodiments, and not include overlapping portions with neighboring patches in other embodiments. Then, at least one patch is analyzed separately from at least some other patches. In some embodiments, neighboring patches may be employed when analyzing a given patch, while in other embodiments, the patch may be analyzed independently of all other patches. The artifact dictionary entries and non-artifact dictionary entries may correspond to a patch size of the patches, with the entries used to identify at least one artifact in the patch being analyzed. After the comparison of the given patch with the dictionary entries, and identification of the artifact, the processing unit 120 may then remove the identified artifact to generate a corrected patch. The processing unit 120 (for example after correcting one or more other patches) may combine the corrected patch with other patches to provide a corrected image.

Figure 3:
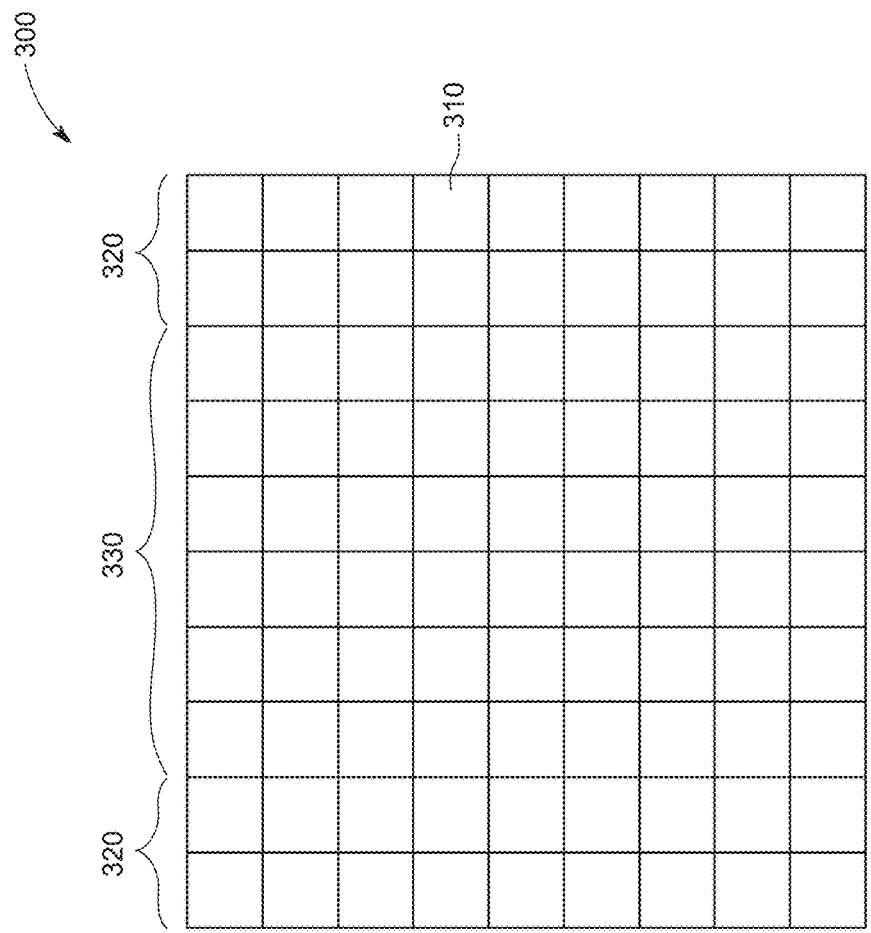
FIG. 3 illustrates a schematic depiction of a patch layout in accordance with various embodiments.

In some embodiments, the processing unit 120 may select artifact dictionary entries with which to analyze a given patch (or patches) based on a location of the given patch. For example, FIG. 3 illustrates a schematic depiction of a patch layout 300. It may be noted that the patch layout 300 is provided by way of example for ease and clarity of illustration, and that various modifications (e.g., to size, shape, location, and/or number of patches) may be made in various embodiments.

As seen in FIG. 3, the patch layout 300 includes patches 310 arranged in a grid pattern. In the example depicted in FIG. 3, the patches 310 do not overlap with neighboring patches. The patch layout 300 includes edge patches 320 and central patches 330. In various embodiments, different patches may be subject to one or more different artifacts based on their location within an image. For example, truncation artifacts may be common at an edge of an image but not in the center of an image. Accordingly, edge patches 320 may be likely subjected to truncation artifacts, while central patches 330 may not be. Thus, the processing unit may select edge patches 320 for analysis using a truncation artifact dictionary, while not analyzing central patches 330 using the truncation artifact dictionary to speed up and/or simplify the artifact identification and removal process.

For each patch, a separate comparison of the patch image to dictionary entries may be performed. For example, an Artifact Dictionary and Non-Artifact Dictionary may have the following entries as summarized in the table below (it may be noted that the dictionaries only have three entries for simplicity of illustration, in practice more entries may be employed):

| Artifact Entry | Non-Artifact Entry |
|---|---|
| A1 | B1 |
| A2 | B2 |
| A3 | B3 |

Different combinations of entries may be compared to a given patch until a closes comparison is identified. For example, if the combination of A1 and B1 provides the closest match to the given patch, artifact entry A1 may be identified as the artifact and removed from the patch to provide a corrected patch that may be combined with other patches to generate a corrected image. It may be noted that, in various embodiments, the processing unit 120 may be configured to identify the at least one artifact using a weighted combination of an entry from the artifact dictionary and an entry from the non-artifact dictionary. For example, where A represents an artifact dictionary entry, and B represents a non-artifact dictionary entry, an image may be compared to a combination C of various dictionary entries, where C is given by $C=\alpha*A+\beta*B$, where $\alpha$ and $\beta$ are weighting coefficients. A least squares fit or other optimization analysis may be performed to determine the best matching combination of entries along with $\alpha$ and $\beta$. The identified artifact entry (e.g., modified by $\alpha$) may then be removed from the image or patch. The larger $\alpha$ (and smaller $\beta$) is indicates a more prevalent effect of an artifact, whereas the smaller $\alpha$ (and larger $\beta$) is indicates a less prevalent effect of an artifact. For an image or patch for which the best fit includes an a of zero, then an artifact represented by the various entries of the artifact dictionary may be understood as not being present.

It may be noted that, in some embodiments, the non-artifact dictionary includes entries corresponding to representations of anatomy. Such entries may be constructed or developed, for example, using images known to be accurate representations from previous clinical studies. In other embodiments, the non-artifact dictionary includes entries corresponding to uncorrelated noise, for example uncorrelated noise with a uniform distribution. The use of uncorrelated noise for non-artifact dictionary entries may help provide entries that are mutually distinctive with respect to the artifact dictionary entries.

For example, in some embodiments where uncorrelated noise is used to construct the entries for the non-artifact dictionary, the processing unit 120 may first divide the initial image into plural patches, and then subtract a mean value of one or more patches to be analyzed for artifacts from the one or more patches. Then, the processing unit 120 may analyze the one or more patches using the artifact dictionary and the non-artifact dictionary after subtracting the mean value.

As indicated herein, the processing unit 120 is configured to control various aspects of the CT acquisition unit 110 and/or to reconstruct an image using information obtained via the CT acquisition unit 110. For example, the processing unit 120 may be configured to reconstruct a CT image using information collected by the CT acquisition unit 110.

The depicted processing unit 120 is operably coupled to the input unit 150, the output unit 140, and the CT acquisition unit 110. The processing unit 120, for example, may receive imaging data or projection data from the CT detector 114. As one more example, the processing unit 120 may provide control signals to one or more aspects of the CT acquisition unit 110, such as the X-ray source 112 and CT detector 114. In various embodiments, the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may be distributed among various units or housings. It may be noted that operations performed by the processing unit 120 (e.g., operations corresponding to process flows or methods discussed herein, or aspects thereof) may be sufficiently complex that the operations may not be performed by a human being within a reasonable time period. For example, the reconstruction of an image, or the analysis of an image (or patches of an image) using dictionary entries as discussed herein, may rely on or utilize computations that may not be completed by a person within a reasonable time period.

The depicted processing unit 120 is configured to control the CT acquisition unit 110 (e.g., by controlling the activation and deactivation of the X-ray source 112) to collect CT imaging information during an imaging scan. The processing unit 120 may also control a longitudinal translation of the CT acquisition unit 110 relative to the object being imaged. For example, the processing unit 120 may control the CT acquisition unit to advance a given distance along the length of an object being imaged as a step or increment between rotations.

In the illustrated embodiment, the processing unit includes a reconstruction module 122, an analysis module 124, an artifact removal module 126, and a memory 128. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

The depicted reconstruction module 122 is configured to reconstruct one or more images using imaging or projection data acquired from the CT detector 114. For example, the reconstruction module 122 may receive imaging information from the CT detector 114 taken over a number of views (e.g., for a full rotation or portion thereof, or for a number of rotations taken at different positions along the length of an object to be imaged) and reconstruct an image to be used for diagnostic purposes. For example, the reconstruction module 122 may reconstruct an initial image from which artifacts will be removed. In various embodiments, the reconstruction module 122 and/or the analysis module 124 may divide an image (e.g., the initial image) into patches.

In the illustrated embodiment, the analysis module 124 is configured to receive an initial image (or portion thereof such as a patch or group of patches) from the reconstruction module 122. The analysis module 124 may then analyze the initial image (or portion thereof) using dictionaries as discussed herein to identify one or more artifacts. An identified artifact may, for example, correspond to a particular entry in an artifact dictionary, or to an entry modified by a weighting coefficient (e.g., a weighting coefficient determined via a least squares analysis).

The depicted artifact removal module 126 is configured to receive one or more identified artifacts from the analysis module 124 and to remove the one or more identified artifacts from the initial image or from a patch of the initial image. For example, a number of artifacts may be removed from plural patches, and the patches may be combined with other patches of the initial image to form a corrected image.

The memory 128 may include one or more computer readable storage media. The memory 128, for example, may store artifact and non-artifact dictionaries, image data corresponding to images generated, results of intermediate processing steps, or the like. Further, the process flows and/or flowcharts discussed herein (or aspects thereof) may represent one or more sets of instructions that are stored in the memory 128 for direction of operations of the system 100.

The output unit 140 is configured to provide information to a user. The output unit 140 may be configured to display, for example, information regarding a detected recurring artifact, or, as another example, one or more images using information obtained during one or more corresponding imaging scans. The output unit 140 may include one or more of a screen, a touchscreen, a printer, or the like.

The input unit 150 may be configured to obtain an input that corresponds to one or more settings or characteristics of a scan to be performed, and to provide the input (or information corresponding to the input) to the processing unit 120, which may use the input to determine, adjust, or select parameters used for performing a scan. The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device.

Figure 4:
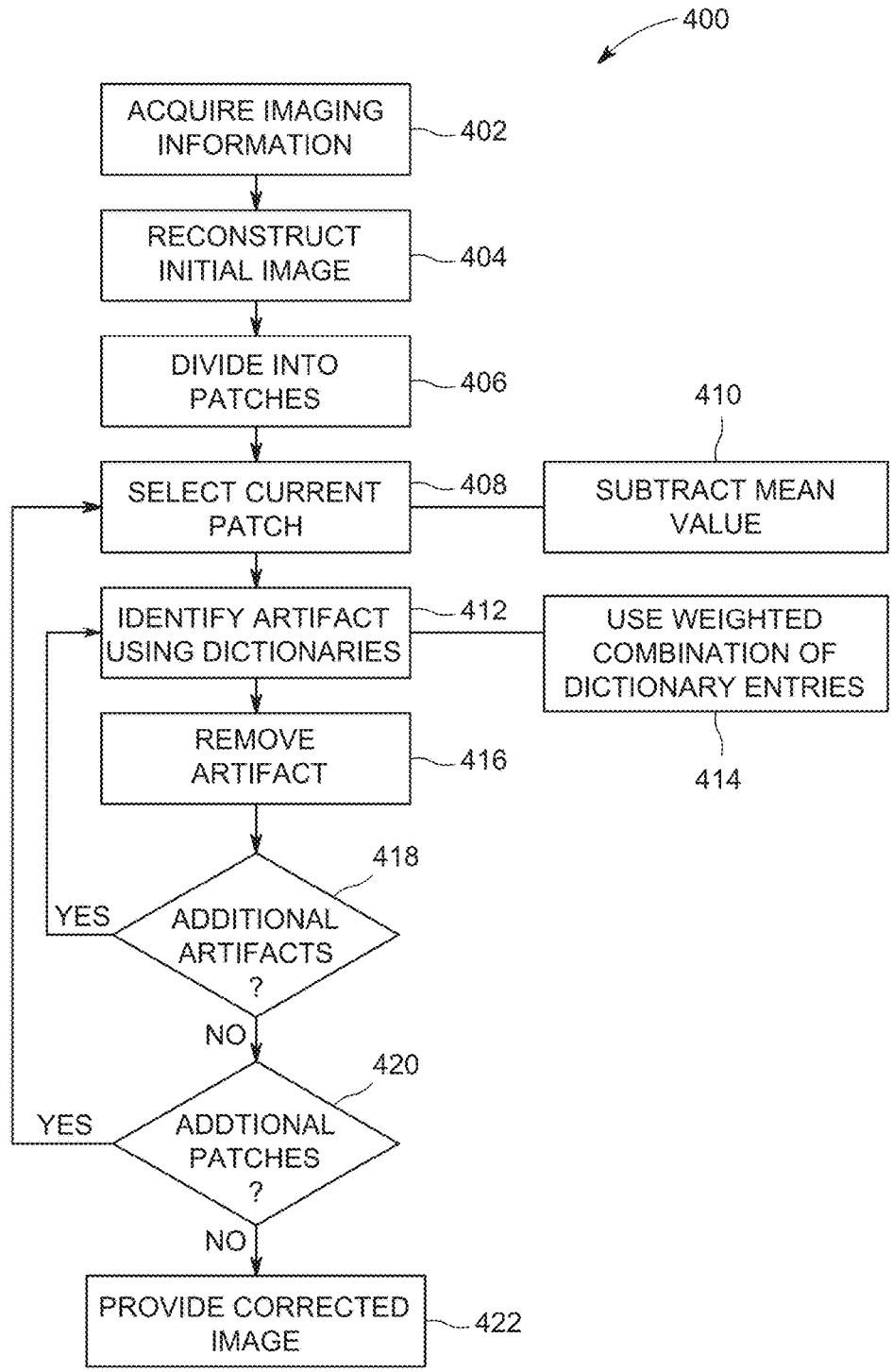
FIG. 4 is a flowchart of a method in accordance with various embodiments.

FIG. 4 provides a flowchart of a method 400 for imaging an object in accordance with various embodiments. The method 400, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be able to be used as one or more algorithms to direct hardware (e.g., one or more aspects of the processing unit 120) to perform one or more operations described herein.

At 402, imaging information (e.g., CT imaging information) is acquired, for example of an acquisition volume of an object. In some embodiments, the CT imaging information may be acquired by one or more processors directly from a CT acquisition unit. In some embodiments, the imaging information may be acquired from a storage device, memory device, and/or network or internet connection. The one or more processors that acquire the imaging information may be integral with an acquisition unit as part of an imaging system located at a single location, or the one or more processors may be located remotely from the acquisition unit.

At 404, an initial image is reconstructed using the imaging information. For example, CT imaging information may be acquired in projection or sinogram space, and the image reconstructed in image space. The reconstructed image may be, for example, in a spatial domain of image space, and represented by a function $p(x, y, z)$, where z is a longitudinal direction, an x-z plane is a coronal plane, a y-z plane is a sagittal plane, and an x-y plane is an axial plane (e.g., a plane oriented normal to an axis passing along the length of an object being imaged).

At 406, the initial image is divided into patches. The size of the patches may be selected to correspond to identifiable artifacts or portions thereof and/or for convenient or efficient processing. In some embodiments patches may overlap to an extent with neighboring patches, while in other embodiments neighboring patches may not overlap.

At 408, a current patch is selected. The current patch may be selected based on a location of the patch. For example, a patch from a portion of an image for which a known artifact is likely to occur may be selected for analysis with respect to the known artifact. In some embodiments, (e.g., embodiments using non-artifact dictionary entries corresponding to uncorrelated noise), a mean value for the patch may be determined and subtracted from the patch at 410 before the patch is analyzed.

At 412, at least one region of the initial image containing at least one artifact is identified, and the at least one artifact is isolated from desired image content using dictionaries. For example, a dual dictionary or discriminatory dictionary including two sub-dictionaries may be employed. One sub-dictionary may be an artifact dictionary having entries corresponding to known, previously studied or documented artifacts. Another sub-dictionary may be a non-artifact dictionary. In some embodiments, the non-artifact dictionary may have entries describing or corresponding to representations of anatomy, while in other embodiments the non-artifact dictionary may have entries corresponding to uncorrelated noise. Entries from the two sub-dictionaries may be combined and compared to the current patch of the initial image, with the artifact entry of the combination providing the best match identified as the artifact. In some embodiments, a weighted combination of dictionary entries may be employed at 414. In such embodiments, the identified artifact may be a weighted modification of the artifact dictionary entry of the combination providing the best match.

At 416, the artifact is removed. For example, the entry of the artifact dictionary of the best matching combination from 412 (or a weighted modification thereof) may be identified as the artifact and subtracted from the patch to provide a corrected patch.

At 418, it is determined if an additional artifact is to be considered for the selected patch. If so, the method 400 returns to 412 and an analysis using an artifact dictionary for the additional artifact is performed. If not, the method 400 proceeds to 420.

At 420, it is determined if an additional patch is to be analyzed. If so, the method 400 returns to 408 with a new patch set as the current patch. If not, the method 400 proceeds to 422.

At 422, a corrected image is provided. For example, the corrected image may be provided by combining patches initially provided from the initial image, including one or more patches that have been corrected.

As discussed herein, various different types of artifacts may be addressed using methods and/or systems disclosed herein. An example approach to removing or mitigating truncation artifacts will now be discussed in further detail. It may be noted that the scanning field of view (SFOV) of a CT system is jointly determined by detector size, x-ray beam collimation, and geometric magnification. When part of the image object goes out of the SFOV (e.g., due to large size of the image object or other constraints), the measured projection data will result in an abrupt change at the SFOV boundary. This abrupt change may be amplified by a filtering process during a filtered backprojection (FBP) reconstruction. As a result, the filtered signal values at or near the SFOV boundary are significantly elevated. After the backprojection step is implemented, blooming artifacts will be present in the reconstructed FBP CT image because its pixel values near the truncation locations are erroneously elevated.

To reduce truncation artifacts, a variety of data extrapolation methods have been developed to enable a smoother transition of the object signal across the SFOV boundary. Generally, the key of extrapolation-based truncation artifact reduction methods is to compensate the missing projection data such that the projection data falls smoothly to zero. These previous correction methods are used in the projection domain and are not applicable when the projection data are not available.

In various embodiments disclosed herein, CT truncation artifacts may be addressed directly in the image domain. An image contaminated with a truncation artifact may be decomposed into two parts, one with reduced truncation artifacts and the other one containing only truncation artifacts, or substantially only truncation artifacts. The decomposition may be accomplished using a discriminative dictionary comprised of a sub-dictionary featuring truncation artifacts and a counterpart sub-dictionary with randomly distributed intensities. When these two sub-dictionaries are properly constructed, anatomical structures in the original image represented in the artifact sub-dictionary are vanishingly negligible, and the truncation artifacts represented in the counterpart sub-dictionary are also vanishingly small. Accordingly, provided a properly constructed discriminative dictionary is used, the truncation artifact-contaminated image may be decomposed into two mutually exclusive images, allowing truncation artifacts to be separated from anatomical structures. Through both phantom and/or in vivo human subject studies, a proper discriminative dictionary may be constructed, and used to separate truncation artifacts from anatomical structures.

Next, the dictionary representation of images will be discussed. To obtain a digital image representation of an analog image function $I(\vec{x})$, a series of basis functions $b_i$ (i=1, 2, ..., N) may be used to expand an image function as follows:

$$I(\vec{x}) \approx \sum_{i=1}^{N} I_i(\vec{x}) b_i. \qquad \text{Eq. 1}$$

The expansion coefficients in Eq. 1 may be lexicographically arranged to generate a column vector $\vec{I}=(I_1, I_2, \ldots, I_N)$, which may be referred to as the vectorized digital representation of the analog image function $I(\vec{x})$. Different basis functions, such as wavelet based and framelet based have been constructed. Traditionally, orthonormal bases have been used to represent an image. However, the use of orthonormality may not lead to a sparse representation of the image. Thus, an over-complete basis (e.g., a group of signifcantly redundant basis vectors) and a matching pursuit algorithm may be used to achieve sparse enconding of an image. For example, a group of M redundant bases vectors $(\vec{b}_1, \vec{b}_2, \ldots \vec{b}_M)$ may form a dictionary $D \equiv (\vec{b}_1 | \vec{b}_2 | \ldots | \vec{b}_M)$, and each column vector $\vec{b}_j$ may be referred to as an atom of the dictionary. Using the dictionary D, the image vector $\vec{I}$ may be written as a linear combination of these basis vectors:

$$\vec{I} = \sum_{j=1}^{M} \alpha_j \vec{b}_j = D\vec{\alpha}. \qquad \text{Eq. 2}$$

An approximate sparse representation of an image in terms of a known dictionary D may be found by solving the following constrained optimization problem:

$$\vec{\alpha}^* = \underset{\vec{\alpha}}{\operatorname{argmin}} \|\vec{I} - D\vec{\alpha}\|_2^2, \text{ s.t. } \|\vec{\alpha}\|_0 < L, \qquad \text{Eq. 3}$$

where $\|\cdot\|_2$ denotes the Euclidean norm, $\|\cdot\|_0$ denotes the "zero-norm," which measures the total number of non-zero components in a vector, and L is a parameter determining the desired maximum number of atoms from the dictionary D to approximate the image $\vec{I}$. In a specific application, the most nontrivial task is to construct a dictionary such that an image $\vec{I}$ may be represented with $\vec{\alpha}$ with the fewest number of nonzero elements, or in other words, to seek a dictionary D to achieve sparse representation of the image. Such a construction is discussed in the following.

Before introducing an algorithm to reduce CT truncation artifacts using a discriminative dictionary, an additional technical idea and associated mathematical notation are briefly discussed. Because the size of a CT image is usually large, the direct computation of its sparse representation using a dictionary may be computationally expensive. To divide the problem into smaller problems that are manageable, for example, with a personal computer, an image may be decomposed into many smaller patches $\vec{P}_k = R_k \vec{I}$, where $R_k$ is a patch extraction matrix and k denotes the index of each patch. After sparse representation, these individual patches may be recombined to restore the original image. Therefore, the dictionary used in the sparse representation is composed of atoms with the same size of the patches. For example, the patch size may be set to 40×40 pixels, and the center-to-center distance between two neighboring patches may be set to 10 pixels, providing an example of patches that overlap with their neighbors.

Next, truncation artifacts reduction via a discriminative dictionary representation (TARDDR) algorithm will be discussed. When an image patch $\vec{I}$ is contaminated with truncation artifacts, the image may be decomposed into a corrected image $\vec{I}_c$ and an artifact-only image $\vec{I}_a$:

$$\vec{I} = \vec{I}_c + \vec{I}_a. \qquad \text{Eq. 4}$$

This decomposition may be quite arbitrary if no further constraint is introduced. In various embodiments, two mutually exclusive sparse representations with two different sub-dictionaries may be used to achieve this decomposition. The first sub-dictionary $D_a$, is constructed to represent only the truncation artifacts, and the other sub-dictionary $D_n$, is constructed to represent the non-artifact components of the image. The two discriminative sub-dictionaries $D_a$ and $D_a$ are composed by atoms of the same size as the image patch $\vec{I}$. The term "exclusive sparse representation" as used herein means that the truncation artifacts cannot be sparsely represented in terms of the atoms in $D_n$, and the non-artifact image components cannot have sparse representation in terms of the atoms in $D_a$. In various embodiments, the artifact sub-dictionary $D_a$ may be constructed by utilizing the exponent decay feature of the truncation artifact along the radial direction of axial CT images, and the counterpart sub-dictionary $D_n$ may be composed of atoms with uniformly distributed random intensities to ensure its large morphological discrepancy with resect to $D_a$.

As truncation artifacts may be present only at peripheral regions of an SFOV, correction of truncation artifacts may be performed only at those local regions to save computational cost. In some embodiments, a distance constrained region growing (DCRG) method may be used to automatically segment the truncation artifact-contaminated patches. Another preprocessing step may be performed, namely the segmenting and replacement of boney structures and air in the original image. Highly x-ray attenuating boney structures may have similar pixel values to those of truncation artifacts and thus may potentially be represented by artifact sub-dictionary $D_a$. The pixel values outside the circular SFOV is much smaller than those of soft tissue, which may potentially violate the exponential decay assumption used in constructing $D_a$. The replacement of these two types of pixels may be performed via the following:

$$I_i' = \begin{cases} I_{h'}, & I_i > I_h \\ I_{l'}, & I_i < I_l \\ I_i, & \text{otherwise.} \end{cases} \quad \text{Eq. 5}$$

Figure 5:
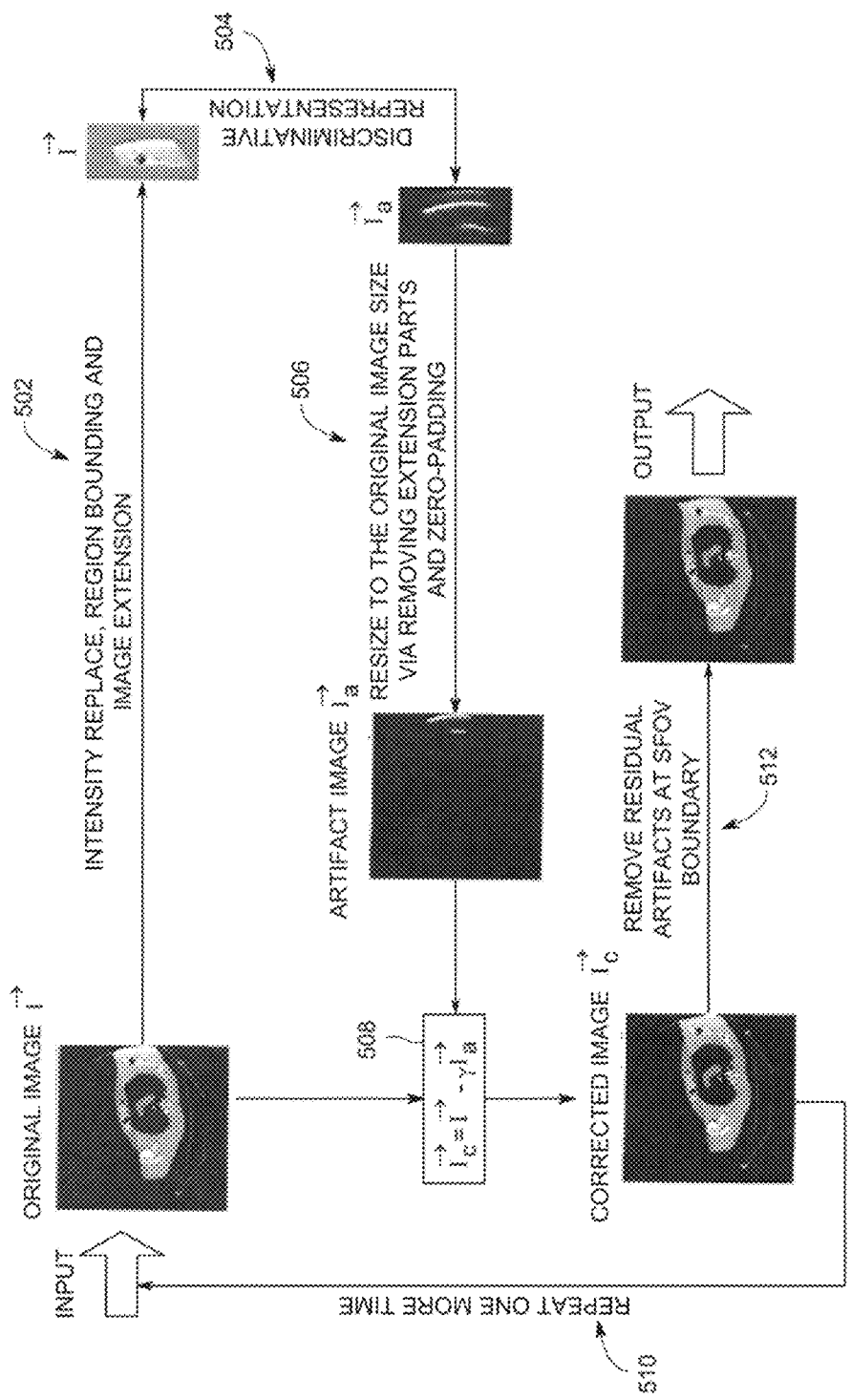
FIG. 5 is a schematic depiction of a workflow in accordance with various embodiments.

Put another way, for those pixels with their values greater than a high threshold $I_h$ or smaller than a low threshold $I_l$, they will be replaced by present values $I_{h'}$ or $I_{l'}$. After the preprocessing operations, the following sparse decomposition problem may be solved for each image patch:

$$\{\vec{\alpha}_{c,k}^*, \vec{\alpha}_{a,k}^*\} = \underset{\vec{\alpha}_{c,k}, \vec{\alpha}_{a,k}}{\operatorname{argmin}} \left\| \vec{P}_k' - D_n \vec{\alpha}_{c,k} - D_a \vec{\alpha}_{a,k} \right\|_2^2, \quad \text{Eq. 6}$$

$$\text{s.t. } \|\vec{\alpha}_{c,k}\|_0 + \|\vec{\alpha}_{a,k}\|_0 < L,$$

Where $\vec{P}_k'$ denotes the kth patch fetched from the preprocessed image $\vec{I}'$ using the patch extraction operator $R_k$. Although this constrained optimization problem is not convex, the matching pursuit (MP) algorithm (also known as the Greedy Algorithm) and its improved version, the orthogonal MP (OMP) algorithm, may be reliable and efficient algorithms to solve this problem. For example, in various embodiments, the OMP algorithm may be used to numerically solve the non-convex optimization problem. An artifact-only image $\vec{I}_a'$ may be built as follows:

$$\vec{I}_a' = \frac{\sum_k R_k^T D_a \vec{\alpha}_{a,k}^*}{\sum_k R_k^T R_k}, \quad \text{Eq. 7}$$

where $R_k^T$ denotes the transpose of the patch-extraction matrix Rk. After this artifact-only image $\vec{I}_a'$ is generated, the corrected image may be generated by subtracting the artifact image from the original image as follows:

$$\vec{I}_c = \vec{I} - \gamma \vec{I}_a', \quad \text{Eq. 8}$$

where γ is a numerical weighting factor to reduce potential over separation due to the fact that the sparse encoding is an approximation method. To eliminate the residual artifacts after one single correction, the correction procedure may be repeated by using the corrected image as the input image for the second pass. After a predetermined number of passes (e.g., two) are performed, residual artifacts in the form of a bright arc at the boundary of the SFOV may be removed by setting its pixel intensity to that of air. FIG. 5 presents a summary of a work flow of a TARDDR algorithm.

As seen in FIG. 5, an original image is input, and at 502, intensity replacements, regions bounding and image extension are performed. Then, at 504, discriminative representation is performed. Next, at 506, an artifact image is resized to an original image size via removing extension parts and zero-padding. At 508, a corrected image is generated by subtracting an artifact component. The corrected image may be subject to one or more additional passes at 510. Once the additional passes are complete, residual artifacts may be removed at the SFOV boundary to provide a final corrected image as an output.

Next, the construction of the discriminative dictionary ($D=D_n$, $D_a$) will be discussed. Generally, the artifact sub-dictionary $D_a$ should give a good representation of artifact features, and atoms in $D_a$ and its counterpart sub-dictionary $D_n$ should have features that are mutually distinctive to each other. In some embodiments, use of normal human anatomical features to construct $D_n$ may lead to erroneous representations of truncation artifacts, because some anatomical structure may have similar morphologies to those of the artifacts. Accordingly, in some embodiments, patches of an image containing only uncorrelated noise with a uniform distribution in the range of [0, 1] may be tiled to form $D_n$.

The atoms in the artifacts sub-dictionary $D_a$ may be constructed to reflect the characteristic intensity distributions of typical CT truncation artifacts, which may appear near the peripheral region of the SFOV and decay towards the center of the image. The decay in pixel intensity may be modeled as the following exponential function:

$$f(r) = e^{-\beta(R-r)/R}, \quad \text{Eq. 9}$$

where β is a dimensionless decay parameter, r is the radial distance to the iso-center of the scanner, and R is the radius of the SFOV. Based on observation and modeling of truncation artifacts, it has been found that $\beta \in [3, 7]$ would be robust for truncation artifacts observed in practice. Based on the model in Eq. 9, a total of thirty 512×512 images with endocentric circles with different decay parameters β=(3, 4, 5, 6, 7, 8) may be used to generate atoms of the sub-dictionary $D_a$.

Next, region bounding using DCRG will be discussed. As discussed herein, DCRG-based region bounding may be used to automatically identify local regions contaminated by truncation artifacts and reduce computational cost. Those pixels in an arc along the boundary of the SFOV having intensities higher than preset threshold may be tagged as a group of seed points, which may be sorted from large to small and saved in a queue. In each DCRG iteration, the largest element may be removed from the queue and tagged as an artifact point $I_s$. For every pixel $I_n$ in an immediate neighborhood of the current $I_s$, as long as it is greater than the threshold $I_{rg}$, the pixel may be penalized by its distance to $I_s$ as follows:

$$I_n' = I_n - ae^{D_{s,n}/b}, \quad \text{Eq. 10}$$

where $D_{s,n}$ denotes the distance between $I_s$ and $I_n$, and a and b are two control parameters. After this penalty, $I_n'$ is still greater than the threshold $I_{rg}$, its location is saved in a pool labeled as "pixels contaminated by truncation artifacts." This process is iterated for every seed point in the queue, filling the pool with every artifact-containing pixel in the image. The pool is used as a mask to automatically segment location regions for TARDDR processing. In various embodiments, parameters a and b may be empirically chosen to be 10 and 20, respectively, which were found to be robust to produce reliable artifact maps for both phantom and human subject studies.

It may be noted that the TARDRR approach discussed herein achieves CT truncation artifact correction via a discriminative dictionary representation of a CT image. The discriminative dictionary includes an artifact sub-dictionary and a non-artifact sub-dictionary, each of which is composed of atoms with distinctive features to the other sub-dictionary. Such an approach (and other approaches disclosed herein) may operate purely in the image domain and not require the availability of projection data. Accordingly, such approaches may be applied retrospectively to DICOM CT images acquired from different scanner models. For the TARDRR approach, the only piece of a priori knowledge required is the size of the SFOV, which may be available in DICOM header. It may be noted that, in embodiments where a noise model (e.g., a uniform white noise model) is used to create the non-artifact dictionary, the non-artifact dictionary need not perfectly represent all the anatomical information of the scanned object. Instead the corrected image may be given by the difference between the original image and the artifact image rather than an image represented by the non-artifact sub-dictionary.

Figure 6:
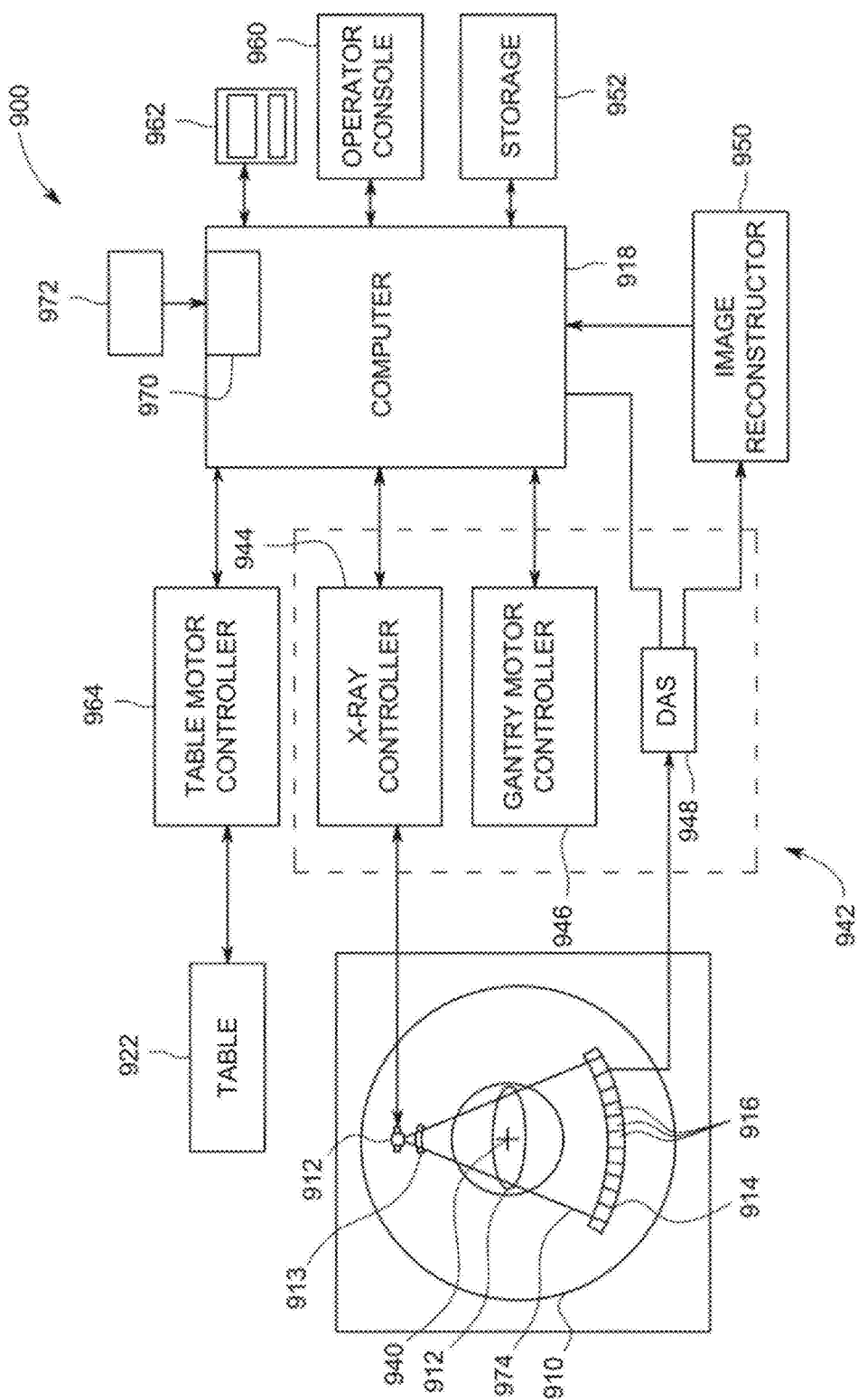
FIG. 6 is a schematic block diagram of an imaging system in accordance with various embodiments.

Various methods and/or systems (and/or aspects thereof) described herein may be implemented using a medical imaging system. For example, FIG. 6 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter are provided proximate the X-ray source 912. In various embodiments, the source collimator 913 may be configured to provide wide collimation as discussed herein. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

The depicted detector array 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 6 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 120 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An imaging system comprising:
a computed tomography (CT) acquisition unit comprising an X-ray source and a CT detector configured to collect CT imaging data of an object to be imaged, the X-ray source and CT detector configured to be rotated relative to the object to be imaged and to collect a series of projections of the object as the X-ray source and CT detector rotate relative the object to be imaged; and
at least one processor operably coupled to the CT acquisition unit, the at least one processor configured to:
reconstruct an initial image using the CT imaging information, the initial image including at least one object representation portion and at least one artifact portion;
identify at least one region of the initial image containing at least one artifact, and isolate the at least one artifact from desired image content by analyzing the initial image using an artifact dictionary and a non-artifact dictionary, the artifact dictionary including entries describing corresponding artifact image portions, the non-artifact dictionary including entries defining corresponding non-artifact image portions, wherein the non-artifact dictionary includes entries corresponding to true or accurate representations of anatomy and entries corresponding to random or uniformly distributed noise; and remove the at least one artifact from the initial image to provide a corrected image.

2. The imaging system of claim 1, wherein the at least one processor is configured to identify the at least one artifact using a weighted combination of an entry from the artifact dictionary and an entry from the non-artifact dictionary.

3. The imaging system of claim 1, wherein the at least one processor is configured to:
divide the initial image into plural patches;
subtract a mean value of at least one patch from the at least one patch; and
analyze the at least one patch using the artifact dictionary and non-artifact dictionary after subtracting the mean value from the at least one patch.

4. The imaging system of claim 1, wherein the at least one processor is configured to:
divide the initial image into plural patches;
analyze at least one patch separately from at least some of the other patches, wherein the artifact dictionary entries and the non-artifact dictionary entries correspond to a patch size of the plural patches, to identify at least one artifact in the at least one patch;
remove the at least one artifact from the at least one patch to generate at least one corrected patch; and
combine the at least one corrected patch with additional patches to provide the corrected image.

5. The imaging system of claim 4, wherein the at least one processor is configured to select non-artifact dictionary entries with which to analyze the at least one patch based on a location of the at least one patch.

6. A method comprising:
acquiring, with a computed tomography (CT) acquisition unit comprising an X-ray source and a CT detector configured to collect CT imaging data, imaging information of an acquisition volume of an object;
reconstructing, with at least one processor, an initial image using the imaging information, the initial image including at least one object representation portion and at least one artifact portion;
identifying, with the at least one processor, at least one region of the initial image containing at least one artifact, and isolating the at least one artifact from desired image content by analyzing the initial image using an artifact dictionary and a non-artifact dictionary, the artifact dictionary including entries describing corresponding artifact image portions, the non-artifact dictionary including entries defining corresponding non-artifact image portions, wherein the non-artifact dictionary includes entries corresponding to true or accurate representations of anatomy and entries corresponding to random or uniformly distributed noise; and
removing, with the at least one processor, the at least one artifact from the initial image to provide a corrected image.

7. The method of claim 6, wherein identifying the at least one artifact comprises identifying the at least one artifact using a weighted combination of an entry from the artifact dictionary and an entry from the non-artifact dictionary.

8. The method of claim 6, further comprising:
dividing the initial image into plural patches;
subtracting a mean value of at least one patch from the at least one patch; and
analyzing the at least one patch using the artifact dictionary and non-artifact dictionary after subtracting the mean value from the at least one patch.

9. The method of claim 6, further comprising:
dividing the initial image into plural patches;
analyzing at least one patch separately from at least some of the other patches, wherein the artifact dictionary entries and the non-artifact dictionary entries correspond to a patch size of the plural patches, to identify at least one artifact in the at least one patch;
removing the at least one artifact from the at least one patch to generate at least one corrected patch; and
combining the at least one corrected patch with additional patches to provide the corrected image.

10. The method of claim 9, further comprising selecting non-artifact dictionary entries with which to analyze the at least one patch based on a location of the at least one patch.

11. A tangible and non-transitory computer readable medium comprising one or more computer software modules configured to direct one or more processors to:
acquire, with a computed tomography (CT) acquisition unit comprising an X-ray source and a CT detector configured to collect CT imaging data, imaging information of an acquisition volume of an object;
reconstruct an initial image using the imaging information, the initial image including at least one object representation portion and at least one artifact portion;
identify at least one region of the initial image containing at least one artifact, and isolate the at least one artifact from desired image content by analyzing the initial image using an artifact dictionary and a non-artifact dictionary, the artifact dictionary including entries describing corresponding artifact image portions, the non-artifact dictionary including entries defining corresponding non-artifact image portions, wherein the non-artifact dictionary includes entries corresponding to true or accurate representations of anatomy and entries corresponding to random or uniformly distributed noise; and
remove the at least one artifact from the initial image to provide a corrected image.

12. The tangible and non-transitory computer readable medium of claim 11, wherein the one or more computer software modules are further configured to direct the one or more processors to identify the at least one artifact using a weighted combination of an entry from the artifact dictionary and an entry from the non-artifact dictionary.

13. The tangible and non-transitory computer readable medium of claim 11, wherein the one or more computer software modules are further configured to direct the one or more processors to:
divide the initial image into plural patches;
analyze at least one patch separately from at least some of the other patches, wherein the artifact dictionary entries and the non-artifact dictionary entries correspond to a patch size of the plural patches, to identify at least one artifact in the at least one patch;
remove the at least one artifact from the at least one patch to generate at least one corrected patch; and
combine the at least one corrected patch with additional patches to provide the corrected image.

14. The tangible and non-transitory computer readable medium of claim 11, wherein the one or more computer software modules are further configured to direct the one or more processors to select non-artifact dictionary entries with which to analyze the at least one patch based on a location of the at least one patch.

15. An imaging system comprising:
a computed tomography (CT) acquisition unit comprising an X-ray source and a CT detector configured to collect CT imaging data of an object to be imaged, the X-ray source and CT detector configured to be rotated relative to the object to be imaged and to collect a series of projections of the object as the X-ray source and CT detector rotate relative the object to be imaged; and
at least one processor operably coupled to the CT acquisition unit, the at least one processor configured to:
reconstruct an initial image using the CT imaging information, the initial image including at least one object representation portion and at least one artifact portion;
divide the initial image into patches;
analyze at least one patch separately from the at least some of the other patches to isolate at least one artifact from desired image content by analyzing the at least one patch using an artifact dictionary and a non-artifact dictionary, the artifact dictionary including entries describing corresponding artifact image portions, the non-artifact dictionary including entries defining corresponding non-artifact image portions, wherein the non-artifact dictionary includes entries corresponding to true or accurate representations of anatomy and entries corresponding to random or uniformly distributed noise; and
remove the at least one artifact from the initial image to provide a corrected image.

\* \* \* \* \*

UNITED STATES PATENT AND TRADEMARK OFFICE
CERTIFICATE OF CORRECTION

PATENT NO. : 10,013,780 B2
APPLICATION NO. : 15/056657
DATED : July 3, 2018
INVENTOR(S) : Jiang Hsieh et al.

Page 1 of 1

It is certified that error appears in the above-identified patent and that said Letters Patent is hereby corrected as shown below:

In the Specification

Column 1, Line 4:
Insert:
--REFERENCE TO GOVERNMENT RIGHTS
This invention was made with government support under EB009699 awarded by the National Institutes of Health. The government has certain rights in the invention.--.

Signed and Sealed this
Twenty-ninth Day of December, 2020

Andrei Iancu
*Director of the United States Patent and Trademark Office*